United States Patent [19]

Sweeney et al.

[11] Patent Number: 5,383,908
[45] Date of Patent: Jan. 24, 1995

[54] DEFIBRILLATION SYSTEM HAVING INNOMINATE VEIN ELECTRODE AND METHOD FOR ITS USE

[75] Inventors: Michael B. Sweeney, Menlo Park, Calif.; Debra S. Echt, Nashville, Tenn.

[73] Assignee: Ventritex, Inc., Sunnyvale, Calif.

[21] Appl. No.: 79,069

[22] Filed: Jun. 16, 1993

[51] Int. Cl.⁶ ............................................. A61N 1/39
[52] U.S. Cl. ........................................................ 607/5
[58] Field of Search ......................... 607/4, 5, 122, 129

[56] References Cited

U.S. PATENT DOCUMENTS

| | | | |
|---|---|---|---|
| Re. 27,757 | 9/1973 | Mirowski | 128/419 |
| 3,942,536 | 3/1976 | Mirowski et al. | 128/419 |
| 4,603,705 | 8/1986 | Speicher et al. | 128/786 |
| 4,662,377 | 5/1987 | Heilman et al. | 128/419 |
| 4,727,877 | 3/1988 | Kallok | 128/419 |
| 4,817,608 | 4/1989 | Shapland et al. | 128/419 |
| 4,827,932 | 5/1989 | Ideker et al. | 128/419 |
| 4,944,300 | 7/1990 | Saksena | 128/419 |
| 4,953,551 | 9/1990 | Mehra et al. | 128/419 |
| 5,007,422 | 4/1991 | Pless et al. | 128/419 |
| 5,269,319 | 12/1993 | Schulte et al. | 128/786 |

OTHER PUBLICATIONS

"Cardiac Pacing—Comparison of Defibrillation Efficacy in Humans Using a New Catheter and Superior Vena Cava Spring–Left Ventricular Patch Electrodes" Winkle, et al, JACC, vol. 11, No. 2, (Feb. 1988) pp. 365–370.

*Primary Examiner*—William E. Kamm
*Attorney, Agent, or Firm*—Mark J. Meltzer; Steven M. Mitchell

[57] ABSTRACT

An electrode configuration for an automatic implantable cardioverter/defibrillator system and method for its use are disclosed. The electrode configuration includes a first catheter transvenously positioned with a first electrode near the distal end of the catheter positioned in the right ventricle of a patient's heart. A second catheter carries second and third electrodes with the second electrode positioned in the superior vena cava region and the third electrode positioned in the left innominate vein. The second and third electrodes of the second catheter are connected together. A fourth electrode at the tip of the first catheter functions as a sensing/pacing electrode. A fifth electrode in the form of a subcutaneous patch is also electrically coupled to the second and third electrodes. The electrode arrangement can be positioned without the need for a thoracotomy. With the method of the invention, the automatic implantable cardioverter/defibrillator senses life-threatening arrhythmic conditions of the heart and issues at least one cardioverting or defibrillating pulse that is applied between the right ventricular electrode and the connected superior vena cava, innominate vein and subcutaneous patch electrodes. The invention provides preferential steering of discharge current through the septum between the right and left ventricles of the heart. The first catheter may also include a pacing tip.

21 Claims, 3 Drawing Sheets

DEFIBRILLATION SYSTEM HAVING INNOMINATE VEIN ELECTRODE AND METHOD FOR ITS USE

FIELD OF THE INVENTION

The present invention relates generally to implantable cardiac stimulation devices, and more specifically to a novel electrode arrangement and method of effecting cardioversion with an automatic implantable system.

BACKGROUND OF THE INVENTION

Automatic implantable cardioverter/defibrillators have been under development since at least the late 1960's. Such a device is described in Re. U.S. Pat. No. 27,757 to Mirowski. A more advanced system is disclosed in U.S. Pat. No. 5,007,422 to Pless et al. which is assigned to the assignee of the present invention and which is incorporated herein by reference. While the technology of cardioverter/defibrillators has advanced significantly, a need still exists for improved lead systems.

As used herein, the term cardioversion generally may be defined as the correction of either ventricular tachycardia or ventricular fibrillation by the discharge of electrical energy into the heart (0.1-40 joules when discharged through internal electrodes). Ventricular tachycardia is an abnormally rapid heart rate (120-180 beats per minute) originating in the heart's main pumping chambers (ventricles) which is regular in periodicity and oftentimes is life threatening to the patient. Ventricular fibrillation is generally a more rapid heartbeat disorder, disorganized and irregular, or non-periodic, and is fatal unless corrected within minutes. This can be accomplished by the discharge of electrical energy through the heart. More specific medical terminology often uses the term cardioversion to mean the synchronized delivery of an electrical shock to the heart to correct ventricular tachycardia. Defibrillation, then, is often referred to as the non synchronized delivery of electrical energy to the heart to correct ventricular fibrillation. Internal cardioversion is usually effective with 0.1 to 3 joules of electrical energy when delivered synchronously with the electrical heartbeat. Internal defibrillation requires 5 to 30 or more joules of electrical energy, depending largely on the electrode system and electrical waveform used.

Many different types of electrode systems have been suggested over the years. Numerous ones of such systems utilize wire mesh epicardial patch electrodes which are typically applied to the heart during open chest surgery. One such system is described in U.S. Pat. No. 4,827,932 to Ideker et al. Major surgery of this type carries with it risks to the patient which should be avoided if possible. The above mentioned Mirowski patent describes an electrode arrangement whereby one electrode is formed on the distal end of an intravascular catheter that is positioned within the right ventricle and a second electrode is positioned on the surface of the chest or sutured under the skin of the chest wall or directly to the ventricular myocardium. Mehra et al. disclose a system in U.S. Pat. No. 4,953,551 wherein a first catheter mounted electrode is located in the apex of the right ventricle (RV) and a second electrode carried on the same catheter is located in the superior vena cava (SVC). A third plate or patch electrode is located subcutaneously outside the chest cavity. The SVC and subcutaneous patch electrodes are electrically interconnected and electric shocks are applied to the heart between this electrode pair and the RV electrode. A similar system is described in U.S. Pat. No. 4,662,377 to Hellman et al. Still other systems provide a separate catheter for the SVC electrode along with the catheter for the RV electrode and the subcutaneous patch electrode. Many such systems include a sensing and pacing electrode on the distal tip of the catheter, distal of the RV electrode. In this configuration, the distal tip electrode and the RV electrode are paired for pacing and sensing functions but are electrically isolated for cardioversion and defibrillation.

While the transvenous lead systems described above appear to be effective, it is desirable to improve the control of the flow of electrical current through the heart during a cardioverting or defibrillating shock to reduce the energy threshold at which such shocks are efficacious. By steering more of the cardioversion or defibrillation current through the ventricular septum such improved efficacy can be achieved.

It is an object of the present invention to provide an improved transvenous lead system electrode configuration.

It is a further object of the invention to provide a cardioversion/defibrillation system with a reduced energy threshold for effective cardioversion and defibrillation shocks.

It is also an object of the invention to provide an automatic implantable cardioverter/defibrillator system with an electrode configuration which will increase the current flowing through myocardial tissue during a cardioversion or defibrillation shock.

It is another object of the invention to provide a method of defibrillating a patient's heart using a lead system having a first electrode in the right ventricle and a second electrode pair in the SVC region and in the left innominate vein.

SUMMARY OF THE INVENTION

The present invention provides an implantable cardioverter/defibrillator system having a novel electrode configuration and a method for providing automatic cardioversion/defibrillation utilizing the system of the invention. The invention allows for placement of the electrodes of a cardioversion/defibrillation system without the major surgery of opening the patient's thoracic cavity which is required with some prior art systems and provides more efficient current discharge through the heart tissue. The electrode configuration of the invention includes a first transvenously positioned catheter with a first electrode near the distal end of the catheter positioned in the right ventricle of a patient's heart. A second catheter carries second and third electrodes with the second electrode positioned in the superior vena cava region and the third electrode positioned in the left innominate vein. The electrodes carried on the transvenous catheters are electrically coupled in series to an implantable cardioverter/defibrillator of the type which is now well-known and which delivers cardioverting and defibrillating pulses to the heart thorough the electrodes. In one embodiment of the invention, the first catheter may also carry a sensing/pacing tip at its distal end. In practicing the method of the invention, the automatic implantable cardioverter/defibrillator senses life-threatening arrhythmic conditions of the heart and issues at least one cardioverting or defibrillating pulse that is applied between the right ventricular electrode at one polarity and the electrically connected superior vena cava and innominate vein electrodes at the opposite polarity. The location of the electrode in the left innominate vein causes more of the discharge current to flow through the septum separating the left and right ventricles. This reduces ineffective current flow through the blood pool. By providing this more efficient current flow, the overall energy delivery requirements for effective therapy are reduced.

In an alternate embodiment of the invention, the three electrodes used for cardioversion/defibrillation are carried on a single catheter. In the case of such a catheter which carries a sensing/pacing tip, the catheter is tripolar with a first conductor for the sensing/pacing tip, a second conductor for the right ventricular electrode and a third conductor for the connected superior vena cava electrode and the innominate vein electrode.

In another alternate embodiment of the invention, which may be practiced with either a single or two separate transvenous catheters, a subcutaneous patch electrode is also included with the system. The subcutaneous patch electrode is electrically connected to the cardioverter/defibrillator with the same polarity as the right ventricular and superior vena cava electrodes. It is located outside the thoracic cavity in the vicinity of the left ventricle.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
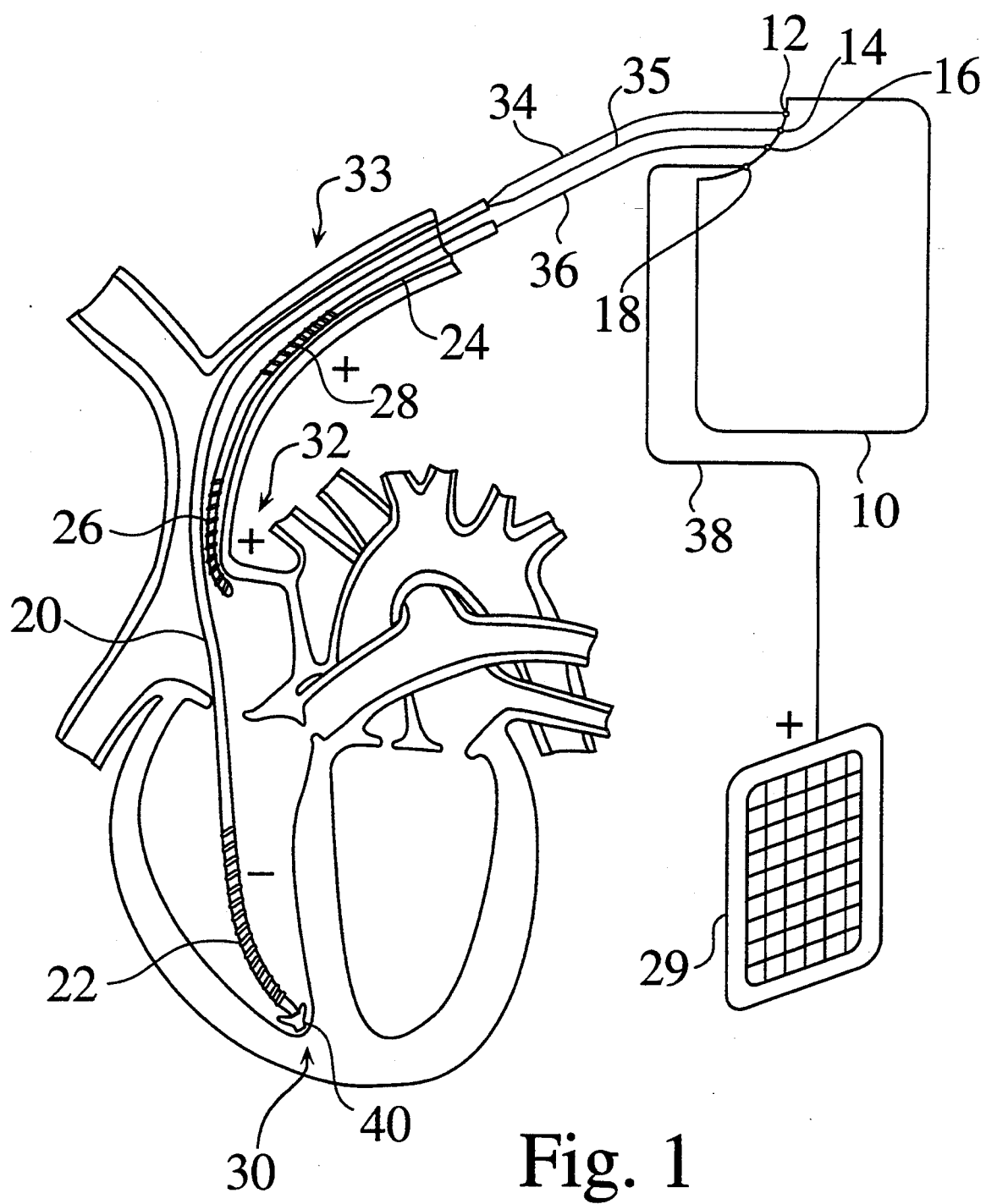
FIG. 1 illustrates the novel electrode arrangement of the present invention in conjunction with an automatic implantable cardioverter/defibrillator system.

The system of the invention will now be discussed with reference to FIG. 1. An automatic implantable cardioverter/defibrillator 10 of the type described in U.S. Pat. No. 5,007,422 is implanted within the abdominal region of the patient and coupled with the electrodes which are transvenously deployed in or near the patient's heart. The cardioverter/defibrillator 10 includes sensing and analysis circuitry, as well as pulse generating circuitry, coupled to the implantable electrodes. The cardioverter/defibrillator 10 senses an arrhythmic condition of the heart and in response to such a condition generates and delivers cardioverting or defibrillating pulses to the heart through the implantable electrodes. The cardioverter/defibrillator 10 includes four terminals 12, 14, 16 and 18 for connecting to various electrodes to provide both sensing and pulse delivery, as will be described in more detail below.

A first catheter lead 20 is coupled to the cardioverter/defibrillator 10 at its proximal end and carries a right ventricular (RV) electrode 22 near its distal end. A second catheter lead 24 is coupled to the cardioverter/defibrillator 10 at its proximal end and carries a superior vena cava (SVC) electrode 26 at its distal end and an innominate vein electrode 28 proximal of the SVC electrode 26. Electrodes 22, 26 and 28 are formed of a close-wound electrically conductive wire forming spring electrodes defined by the perimeter of the catheter. This provides a continuous electrically conductive surface for each electrode which maintains its flexibility while still lowering the impedance of the electrode. Other electrode configurations may be employed such as ring-type electrodes.

The first catheter lead 20 is inserted intravenously, usually from the cephalic, jugular or subclavian vein, to a position such that the RV electrode 22 is positioned in the right ventricle apex 30 of the heart. The lead 20 is anchored in the apex 30 using conventional means such as a tined or a screw tip. The second catheter lead 24 is also inserted intravenously to a position such that the SVC electrode 26 is placed in the superior vena cava region 32 and the innominate vein electrode 28 is positioned in the left innominate vein 33. It should be appreciated that, as the term is used herein, the superior vena cava region 32 includes portions of the right atrium. Thus, the positioning of the SVC electrode 26 may be partially or wholly within the right atrium rather than entirely within the superior vena cava 32. The positioning is determined by the dimensions of the patient's heart and where the patient's physician determines to be the most effective placement to achieve efficient discharge.

The RV electrode 22 is connected via a conductor 34 which extends along the length of the first catheter lead 20 to the first terminal 12 in cardioverter/defibrillator 10. The SVC electrode 26 is connected in series with the innominate vein electrode 28 via a conductor 36 which extends along the length of the second catheter lead 24 to the third terminal 16 in cardioverter/defibrillator 10. The relative impedance of the SVC and innominate vein electrodes can be controlled to direct current flow through the heart. This can be accomplished by providing conductor 36 as a bifilar conductor and inserting a resistive element 27 prior to either the SVC electrode 26 or the innominate vein electrode 28. The length of the SVC and innominate vein electrodes 26, 28 are approximately the same and about 4 to 8 cm. The spacing between the closest portions of the SVC electrode 26 and the innominate vein electrode 28 is approximately 3 to 8 cm.

A flexible patch electrode 29 is electrically connected via a conductor 38 to the cardioverter/defibrillator 10 at its fourth terminal 18, and is subcutaneously positioned outside the thoracic cavity. That is, the patch electrode is connected between the skin and the rib cage. It may be positioned near the left ventricle. However, the precise position for the patch electrode will vary from patient to patient. The patch electrode 29 is a flexible, conformal, generally planar electrode having a metallic mesh on the surface facing the heart, and flexible insulation material on its opposite side. The patch electrode may have a surface area of about 40 sq. cm. although other surface areas may be employed. The conductors 34, 36 and 38 are typically flexible, insulated strands or coils of wire. It is possible to eliminate one of the pulse generator terminals 16 or 18 by connecting conductor 36 with conductor 38 using a "Y" connector.

In addition to the cardioversion and defibrillation electrodes mentioned above, a distal sensing/pacing tip electrode 40 may be included on the first catheter lead 20 distal of the RV electrode 22. The sensing/pacing tip electrode 40 is electrically insulated from the RV electrode 22 and is connected via a conductor 35 which extends along the length of the first catheter lead 20 to the second terminal 14 in cardioverter/defibrillator 10. The sensing/pacing tip electrode 40, in conjunction with the RV electrode 22 and conductors 34 and 35 provide sensing of the heart rate as well as pacing functions. The sensed electrocardiogram (ECG) signals are digitized in the cardioverter/defibrillator 10 and analyzed to identify the presence of an arrhythmic condition in the patient's heart. An appropriate therapy is then determined by the device in response to the sensed ECG signals and predetermined cardioversion/defibrillation pulses are delivered via electrodes 22, 26, 28 and 29.

In operation, the automatic implantable cardioverter/defibrillator 10, after detecting a life-threatening abnormal heart rhythm, step 52, will charge an internal capacitor bank, step 54 and will actuate internal switching circuitry to electrically isolate the sensing/pacing tip electrode 40. It will then deliver a cardioverting or defibrillating pulse from its pulse generator section. In a preferred embodiment of the invention, this pulse is actually a pair of pulses of opposite polarity delivered in close sequence and known as a biphasic pulse. This biphasic pulse is delivered first with terminal 12 at one polarity and terminals 16 and 18 at the opposite polarity for a predetermined time period, step 56, and then the polarities of the terminals are switched, step 58, and the current flows between the electrodes and through the heart tissue in the opposite direction, step 60. The two components of the biphasic pulse are preferably exponentially decaying truncated voltages as is well-known in the art. With the electrode configuration of the invention, the electric current of the high voltage pulses is preferentially directed through the septum thereby providing more efficient, i.e., lower energy or lower voltage, therapy.

Figure 2:
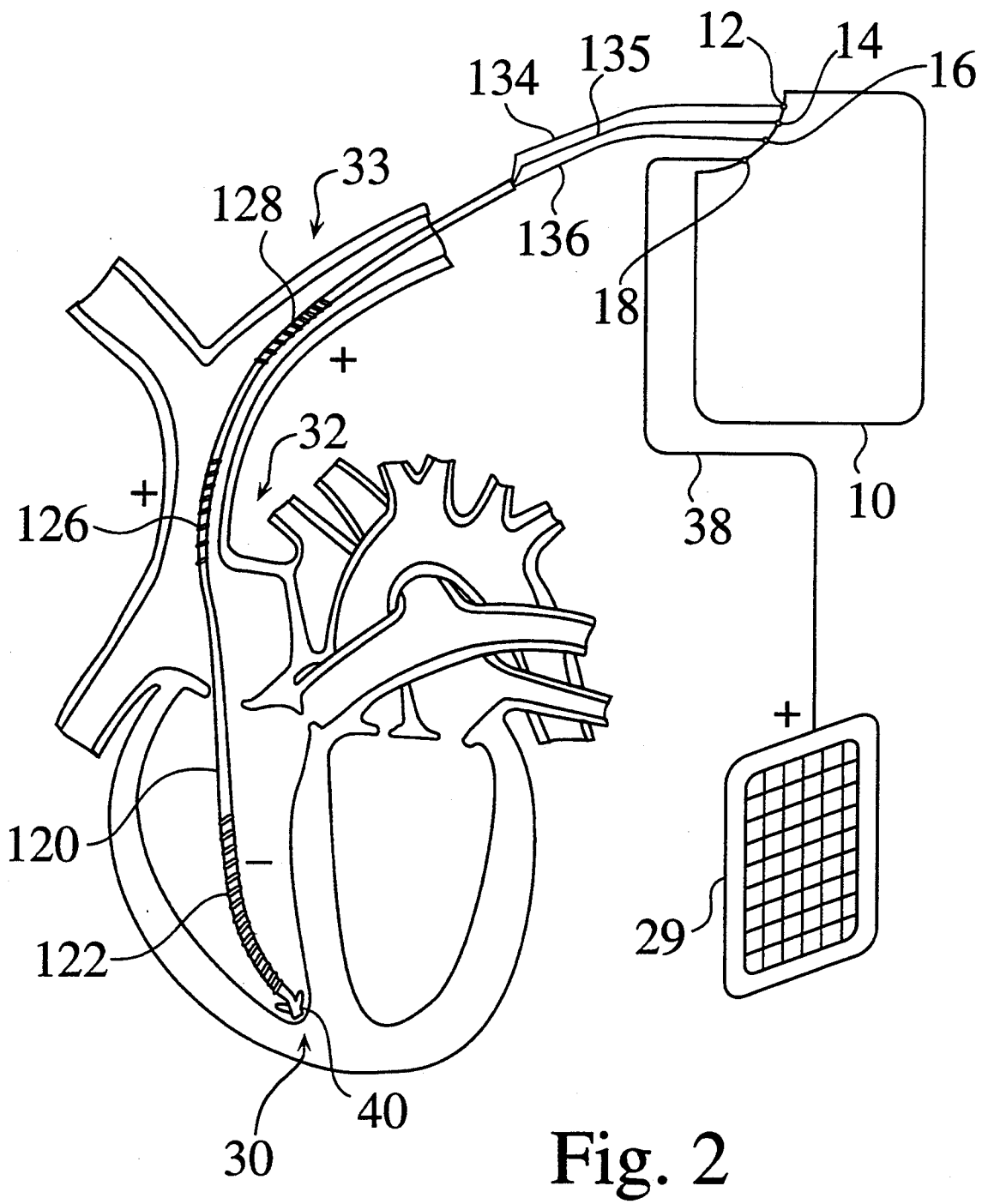
FIG. 2 illustrates an alternative embodiment of the invention in which a unitary transvenous catheter is used.
Figure 3:
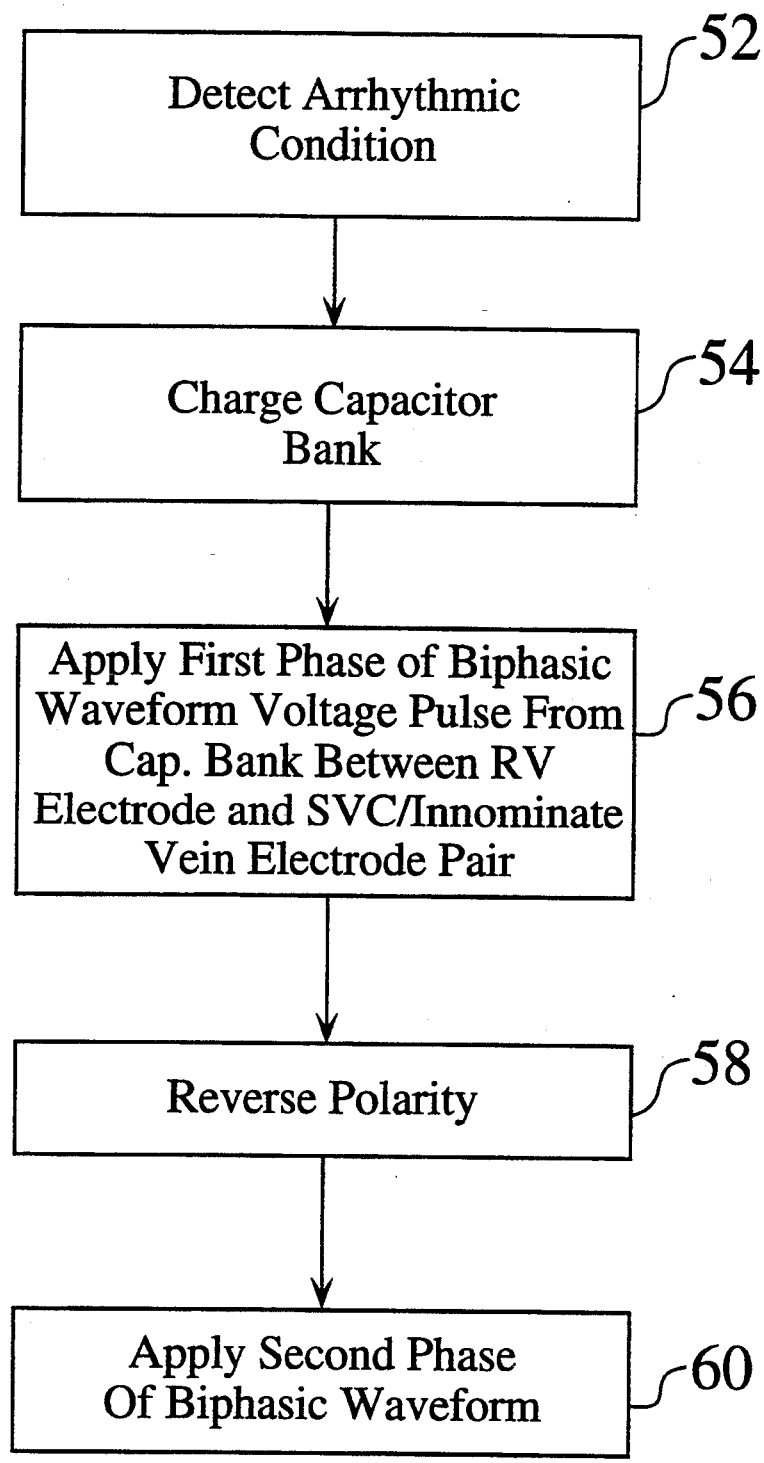
FIG. 3 is a flow diagram showing the steps of the method of operation of the invention.

An alternative embodiment of the invention will now be described with reference to FIG. 2. A unitary catheter lead 120 is coupled to the cardioverter/defibrillator 10 at its proximal end and carries a right ventricular (RV) electrode 122 near its distal end, a superior vena cava (SVC) electrode 126 at an intermediate position and an innominate vein electrode 128 proximal of the SVC electrode 126. Electrodes 122, 126 and 128 are of the same type as described with reference to FIG. 1. The unitary catheter lead 120 is inserted intravenously, in the previously described manner, to a position such that the RV electrode 122 is positioned in the right ventricle apex 30 of the heart. The lead 120 is anchored in the apex 30 using conventional means such as a tined or a screw tip. The SVC electrode 126 is spaced from the RV electrode so that it is positioned in the superior vena cava region 32 and the innominate vein electrode 128 is positioned in the left innominate vein 33.

The RV electrode 122 is connected via a conductor 134 which extends along the length of the unitary catheter lead 120 to the first terminal 12 in cardioverter/defibrillator 10. The SVC electrode 126 is connected in series with the innominate vein electrode 128 via a conductor 136 which extend along a part of the length of catheter lead 120 to the third terminal 16 in cardioverter/defibrillator 10. A distal sensing/pacing tip electrode 140 may be included on catheter lead 120 distal of the RV electrode 122. The sensing/pacing tip electrode 140 is electrically insulated from the RV electrode 122 and is connected via a conductor 135 which extends along the length of catheter lead 120 to the second terminal 14 in cardioverter/defibrillator 10. The other features of this embodiment are the same as those described with respect to the embodiment of FIG. 1.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. An implantable cardioverter/defibrillator system for delivering electrical discharges to the heart of a patient to restore normal cardiac rhythm comprising:
   a pulse generator including sensing means, high energy shock generation means, pacing means and terminals of opposite polarity coupled to said high energy shock generation means;
   a first intravascular catheter insertable within the heart of a patient having a distal first electrode on said first catheter for positioning in the right ventricle, said distal first electrode being connected to a terminal of said pulse generator of one polarity;
   a second intravascular catheter insertable within the superior vena cava the patient having a distal second electrode on said second catheter for positioning in the superior vena cava region and a proximal third electrode on said second catheter spaced from said second electrode for positioning in the left innominate vein;
   electrical conduction means for electrically connecting said second electrode and said third electrode together and to a terminal of said pulse generator of an opposite polarity; and
   discharge means in said pulse generator for supplying electrical energy between said terminals of opposite polarity.

2. The system of claim I wherein said pulse generator emits at least one high energy shock to the implantable electrodes to create an electrical field across the heart between said first electrode and said connected second and third electrodes.

3. The system of claim I wherein each of said electrodes is defined by closely-wound electrically conductive wire about the perimeter of the respective catheter.

4. The system of claim I and further including a subcutaneous patch electrode connected to a terminal of said pulse generator of said opposite polarity.

5. The system of claim I wherein said first catheter further includes a distal tip fourth electrode, wherein said first electrode and said distal tip fourth electrode can provide a sensing input to the cardioverter/defibrillator and a pacing pulse output to the heart.

6. The system of claim 1 wherein said second intravascular catheter further includes a resistive element electrically connected between one of said second electrode or said third electrode and said terminal of said pulse generator of an opposite polarity.

7. A method of cardioverting/defibrillating the heart of a patient comprising the steps of:
   positioning a first electrode within the fight ventricle of the heart;
   positioning a second electrode within the superior vena cava region of the heart;
   positioning a third electrode in the left innominate vein;
   detecting an arrhythmic condition of the heart;
   automatically applying a voltage pulse of a magnitude sufficient to restore normal cardiac rhythm between, firstly, said first electrode, and, secondly, a pair of electrodes comprising said second and third electrodes.

8. The method of claim 7 wherein said step of applying a voltage includes applying said voltage to a subcutaneous patch electrode electrically connected to said pair of electrodes.

9. The method of claim 7 wherein said step of automatically applying a voltage pulse comprises discharging a capacitor between said first electrode and said pair of electrodes for a first predetermined time period, followed by reversing the polarity of said capacitor with respect to said first electrode and said pair of electrodes, then discharging said capacitor between said first electrode and said pair of electrodes for a second predetermined time period, forming an asymmetrical biphasic pulse waveform.

10. An automatic implantable pulse generator system for delivering electrical shocks to the heart of a patient to restore normal cardiac rhythm, the system comprising:
   means for sensing the rhythm of the heart and for detecting abnormal rhythms in need of electrical shock to restore normal rhythm;
   first electrode means adapted to be located in the right ventricle;
   second electrode means adapted to be located in the superior vena cava region;
   third electrode means adapted to be located in the left innominate vein;
   means for connecting together said second and third electrode means; and
   means coupled to said means for detecting abnormal rhythms for delivering electrical cardioverting shocks between said first electrode means and the connected second and third electrode means when said abnormal rhythms are sensed.

11. The system of claim 10 wherein said means for connecting further includes a resistive element electrically connected between one of said second electrode means or said third electrode means and said means for delivering.

12. The system of claim 10 wherein said means for delivering includes a first intravascular catheter and wherein said first electrode means is mounted on said first intravascular catheter.

13. The system of claim 12 wherein said means for delivering further includes a second intravascular catheter and wherein said second and third electrode means are mounted on said second intravascular catheter.

14. The system of claim 12 and further including fourth electrode means mounted on said first intravascular catheter; and means for delivering electrical pacing pulses to the heart through said fourth electrode means.

15. The system of claim 10 wherein said means for delivering further includes an intravascular catheter and wherein said first, second and third electrode means are located on said intravascular catheter.

16. The system of claim 10 and further including fifth electrode means adapted to be located subcutaneously near the left ventricle and electrically connected to said second and third electrode means.

17. The system of claim 16 wherein said fifth electrode means comprises a flexible wire mesh patch.

18. An implantable cardioverter/defibrillator system for delivering electrical discharges to the heart of a patient to restore normal cardiac rhythm comprising:
   a pulse generator having terminals of opposite polarity for generating an electrical shock;
   an intravascular catheter insertable within the heart of a patient;
   a distal first electrode on said catheter for positioning in the right ventricle, said first electrode being connected to a terminal of said pulse generator of one polarity;
   an intermediate second electrode on said catheter for positioning in the superior vena cava region;
   a proximal third electrode on said catheter spaced from said second electrode for positioning in the left innominate vein;
   electrical conduction means for electrically connecting said second and third electrodes together and to a terminal of said pulse generator of an opposite polarity; and
   discharge means in said pulse generator for supplying electrical energy between said terminals of opposite polarity.

19. The system of claim 18 and further including a subcutaneous patch electrode connected to a terminal of said pulse generator of said opposite polarity.

20. The system of claim 18 wherein said first catheter further includes a distal tip fourth electrode, wherein said first electrode and said distal tip fourth electrode can provide a sensing input to the cardioverter/defibrillator and a pacing pulse output to the heart.

21. The system of claim 18 wherein said electrical conduction means includes a resistive element between said second electrode and said third electrode.

* * * * *

UNITED STATES PATENT AND TRADEMARK OFFICE
CERTIFICATE OF CORRECTION

PATENT NO. : 5,383,908
DATED : Jan. 24, 1995
INVENTOR(S) : Michael B. Sweeney, et al It is certified that error appears in the above-indentified patent and that said Letters Patent is hereby corrected as shown below:

Col. 4, Line 41, "30 length of the SVC" should be "length of the SVC"

Col. 6, Claim 1, Line 24 "vena cava the patient" should be "vena cava of the patient"

Col. 6, Claim 7, Line 60 "within the fight ventricle" should be "within the right ventricle"

Signed and Sealed this

Tenth Day of October, 1995

*Attest:*

BRUCE LEHMAN

*Attesting Officer*    Commissioner of Patents and Trademarks